(12) United States Patent
Palumbo et al.

(10) Patent No.: US 6,464,674 B1
(45) Date of Patent: Oct. 15, 2002

(54) ADHESIVE URINE COLLECTOR WITH OPTIMAL APERTURE

(75) Inventors: Gianfranco Palumbo, Bad Homburg (DE); Peter Coles, Kriftel (DE); Vincenzo D'Acchioli, Kelkheim am Taunus (DE); Fabio Cinelli, Bologna (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/720,179

(22) PCT Filed: Jun. 11, 1999

(86) PCT No.: PCT/US99/12957
§ 371 (c)(1),
(2), (4) Date: Dec. 20, 2000

(87) PCT Pub. No.: WO00/00114
PCT Pub. Date: Jan. 6, 2000

(51) Int. Cl.[7] .................................................. A61F 13/15
(52) U.S. Cl. .................................. 604/385.01; 604/317
(58) Field of Search ............................... 604/317, 321, 604/322, 329, 331, 326, 347, 348, 354, 355, 349, 332, 336, 337, 338, 339, 341, 342, 343, 344

(56) References Cited

U.S. PATENT DOCUMENTS

| 3,368,561 | A | | 2/1968 | Ericson et al. | |
|---|---|---|---|---|---|
| 3,577,989 | A | * | 5/1971 | Anderson | 604/348 |
| 3,759,260 | A | | 9/1973 | Nolan et al. | 128/283 |
| 4,804,377 | A | | 2/1989 | Hanifl et al. | 604/352 |
| 5,383,867 | A | | 1/1995 | Klinger | 604/385 |
| 6,007,524 | A | * | 12/1999 | Schneider | 604/327 |

FOREIGN PATENT DOCUMENTS

| EP | 0119143 | * | 3/1984 |
|---|---|---|---|
| GB | 1 078 588 | | 8/1967 |

* cited by examiner

*Primary Examiner*—Jeanette Chapman
(74) *Attorney, Agent, or Firm*—Len W. Lewis; Matthew P. Fitzpatrick; Steven W. Miller

(57) ABSTRACT

This invention relates to a urine management device (10) comprising a bag (11) and a flange (12). The flange (12) comprises adhesive (20) used to attach the device (10) to the uro-genital area of the wearer. The invention resides principally in providing an optimised shape of the aperture (21) of said device (10). One preferred embodiment of the invention is an aperture (21) whose contour is defined by one ellipse in the longitudinal direction, the longitudinal diameter of said ellipse being 2.25 times greater than the transversal diameter.

2 Claims, 2 Drawing Sheets

ADHESIVE URINE COLLECTOR WITH OPTIMAL APERTURE

FIELD OF THE INVENTION

The present invention relates to urine management devices for babies, children or adults, to be adhesively attached in a releasable manner to the uro-genital area of the wearer, said devices being particularly easy to put in place and providing a largely improved performance in collecting urine.

BACKGROUND

Urine management devices are known articles of manufacture that are designed to be worn principally by incontinence sufferers and infants. Such urine management devices are attached to the uro-genital region of the wearer and are intended to entrap and immediately contain urine and other bodily discharges. As a consequence, these devices are functionally effective in lessening epidermal irritation; in preventing contamination of articles such as clothing and bedding; and even in preventing the soiling of the carers themselves.

Typically, the urine management devices are made from a plastic material. For instance, GB 1,092,274 discloses a pediatric urine collector for female use comprising a collector bag of plastic material opening. The base of the opening is provided with a wedge like projection adapted to engage the lower perineal area of the infant. The collector is secured to the body of the wear by adhesive material. GB 2,268,882 discloses a urostomy pouch/bag of plastic material provided with a circular stomal orifice which is surrounded by a first coupling member, by which the pouch can be affixed to a counterpart coupling member, which can be attached to a wearer. The pouch may also be provided for use as a kit further comprising an applicator of super absorbent material which can be injected into the pouch by the use of a plunger. U.S. Pat. No. 4,804,377 discloses a collector for urine specimens from children. The collector comprises a rectangular flange for adhesive attachment, which comprises a round, slightly oval aperture. EP 140 478 discloses a disposable diaper having a water proof barrier preferably polypropylene or polyethylene formed as a flattened bag having a single opening. U.S. Pat. No. 1,092,274 discloses a urine collector for female infants comprising an aperture which is smaller at the bottom end than at the top end and could be described as droplet shaped. U.S. Pat. No. 3,292,626 also discloses a urine collector for female infants comprising a circular or droplet shaped aperture. Chinese patent application CN 1079381 discloses urine bags for infants with circular and elliptical apertures.

Many wearers, who make use of urine management devices have sensitive skin due to their age, whether very old or very young, and furthermore sometimes also suffer from skin irritations. Thus, it is important to minimise skin contact with urine. To this end the aperture should not be chosen too large, since the area of the aperture limits the skin area which potentially comes in contact with urine.

Another problem associated with urine management devices is their behaviour after unintentional detachment and their handling after detachment. Since they regularly are a source of malodour and possibly of leakage, the area of the aperture should not be chosen larger than necessary for good performance.

Thus, considering skin protection and the handling after use, a small aperture is desirable. On the other hand, with regard to the importance of easy and proper placement of the device a larger aperture is desirable.

In attempting to overcome all the aforementioned problems relating to the prior art, it has now been found that adhesive urine management devices can be designed which have excellent ease of placement properties, through the use of a simple, but efficient device. The same design does not only greatly help in placing the device but also assists in handling after detachment.

BRIEF SUMMARY OF THE INVENTION

This invention relates to a urine management device (10) comprising a bag (11) and a flange (12). The flange (12) comprises adhesive (20) used to attach the device (10) to the uro-genital area of the wearer. The invention resides principally in providing an optimised shape of the aperture (21) of said device (10). Preferred embodiments of the present invention regarding the contour of the aperture (21) are: a) a slit like contour, b) an oval contour oriented in said transversal direction, wherein said transversal diameter of the aperture (21) is at least 1.25 times greater than said longitudinal diameter, c) an oval contour oriented in said longitudinal direction, wherein said longitudinal diameter of the aperture (21) is at least 1.25 times greater than said transversal diameter, d) a cross shaped contour. One preferred embodiment of the invention is an aperture (21) whose contour is defined by one ellipse in the longitudinal direction, the longitudinal diameter of said ellipse being at least 2.25 times greater than the transversal diameter.

DETAILED DESCRIPTION OF THE INVENTION

Figure 1:
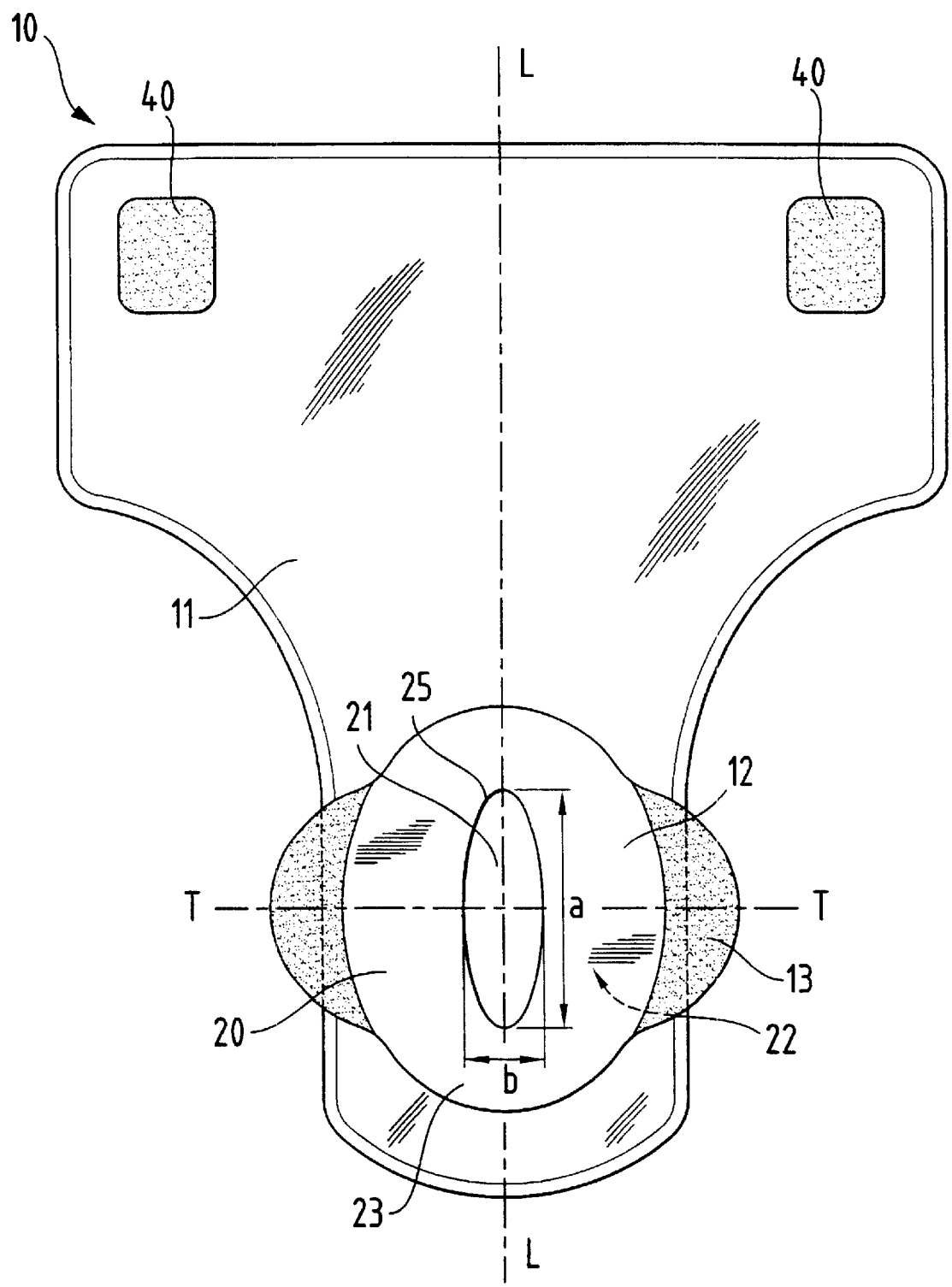
FIG. 1 is a perspective view of one preferred embodiment of the urine management device. L denotes a longitudinal axis, T denotes a transversal axis. a denotes the longitudinal diameter of the aperture, b denotes the transversal diameter of the aperture.

The invention relates to a urine management device (10) as shown in FIG. 1. The device (10) comprises a bag (11) and a flange (12).

Description of the Urine Management Device as a Whole

The term "disposable" as used herein describes devices which generally are not intended to be laundered or otherwise restored or reused (i.e., they are intended to be discarded after a single use and, preferably, to be recycled, composted or otherwise disposed of in an environmentally compatible manner).

Referring now to FIG. 1, there is shown a urine management device (10). Typically disposable urine management devices (10) comprise a bag (11) having an aperture (21) and a flange (12) surrounding the aperture (21) for preferably adhesive attachment to the uro-genital area of a wearer. Any urine management device (10) known in the art can be provided according to the present invention.

The bag (11) as used herein is a flexible receptacle for the containment of discharged urine matter. The bag (11) can be provided in any shape or size depending on the intended use thereof, i.e. whether the device is intended for bedridden patients or active patients suffering from incontinence or for infants. For example, elongated bags which are principally tubular or rectangular are typically utilised by bedridden patients and elderly incontinence sufferers. For more active wearers whether infants or adults, the urine management device should preferably be anatomically shaped such that the device follows the contours of the body and can be worn inconspicuously by the wearer under normal garments.

Particularly, preferred shapes are flat circular and flat T shaped type bags, cone shaped bags, truncated cone shaped bags and pyramidal or truncated pyramidal shaped bags. In a most preferred embodiment of the present invention, the bag (11) has a substantially flat T shape.

In addition, the bag (11) is preferably shaped to fit the uro-genital region of the wearer and ensure good contact between the flange (12) and the skin of the wearer. For example the bag (11) may be provided with a neck portion or conduit.

The bag (11) is preferably designed to provide sufficient volume for urine under a variety of wearing conditions, also when worn by a freely moving, i.e. not bedridden wearer.

The bag (11) is designed to safely contain any entrapped material, typically it will be liquid impermeable, yet it may be breathable. The bag (11) is designed of sufficient strength to withstand rupture in use, also when pressure on the bag (11) is exerted.

According to the present invention, depending on the shape of the bag (11) required, the bag (11) may be provided from a unitary piece of material or from a number of separate pieces of material, which may be identical or different and which are sealed at their respective peripheries.

According to the present invention the bag (11) can comprise one or multiple layers, preferably two or three layers. The layer on the inside of the bag, which will typically at least partially come in contact with urine and or other bodily excretions is called the inner layer. The outermost layer of the bag, which will typically at least partially come in contact with the skin to the wearer and the garments of the wearer, is called the outer layer.

The additional layers of the bag material may be provided from any material, preferably so that the bag is liquid impervious. The layers may in particular comprise any material such as nonwovens or films. In a preferred embodiment of the present invention a laminate may be formed from a nonwoven layer and a film. The laminate can be formed by means known to the man skilled in the art.

Any nonwoven layer can comprise felt fabrics, spunlaced fabrics, fluid jet entangled fabrics, air-laid fabrics, wet-laid fabrics, dry-laid fabrics, melt-blown fabrics, staple fibre carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibres or polymeric binders including natural fibres such as cellulose—wood pulp, cotton, jute, hemp; synthetic fibres such as fibreglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapour such as water vapour in order to avoid the problem of entrapment and condensation of moisture vapour given off by the body of the wearer and thus, the hot, clammy and uncomfortable conditions after a short period of use.

The outer layer of the bag is preferably provided with a hydrophobic fibrous nonwoven layer. Such material layers present an uneven surface to the skin of the wearer and thus reduce significantly the problem of occlusion and greatly improves skin healthiness.

In one preferred embodiment of the present invention the bag comprises two layers. Preferably the outer layer comprises said fibrous hydrophobic nonwoven layer and the inner layer comprises a film.

In yet another preferred embodiment of the present invention, the bag (11) comprises three layers, preferably one film and two nonwoven layers. In an even more preferable embodiment the film is interposed between the two nonwoven layers. This sequence of layers results in a closed fibrous structure, which has a particularly pleasing sensation on contact with the skin of the wearer. In yet another preferred embodiment the inner layer comprises a film and the other two layers comprise nonwovens.

Typically, the nonwoven layer is treated with a surface active material, such as a fluorchemical or other hydrophobic finishings, to provide the requisite hydrophobicity. The nonwoven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example.

The nonwoven layer can also be treated with agents to improve the tactile perceivable softness of the bag. The agents include but are not limited to vegetable, animal or synthetic oils, silicone oils and the like. The presence of these agents are known to impart a silky or flannel-like feel to the nonwoven layer without rendering it greasy or oily to the tactile sense of the wearer. Additionally, surfactant material, including anionic, non-anionic, cationic and non-cationic surfactants, may be added to further enhance softness and surface smoothness.

Furthermore, the nonwoven layer may be impregnated with a lotion to provide desirable therapeutic or protective coating lotion benefits. The lotion is transferable to the skin of the wearer by normal contact and wearer motion and/or body heat. Generally, mineral oil in the form of a lotion is recognised as being effective in imparting a soothing, protective coating to the skin of the wearer. It is also possible to impregnate the nonwoven layer with a solid oil phase of cream formulation or to incorporate into the nonwoven layer an array of pressure- or thermal- or hydrorupturable capsules containing for example, baby oil.

In one embodiment of the present invention the bag (11) may contain absorbent material . The absorbent material may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The absorbent material may be positioned in the bag (11) in any suitable manner. For example, the absorbent material may be loosely arranged within the bag (11) or may be secured to the inner layer of the bag (11). Any known techniques for securing absorbent material to nonwoven and film substrates may be used to secure the absorbent material to the inner layer of the bag (11). The absorbent material may also be arranged to have any desired shape or configuration (e.g., rectangular, oval, circular, etc.).

In the embodiment shown in FIG. 1 the outer surface of bag (11) is provided with patches of adhesive (40) for securing the bag (11) to the body of the wearer. Preferably, the patches of adhesive (40) are positioned on the outer surface of bag (11) such that they are secured to the abdomen of the wearer in use. Any number, size and shape of adhesive patches (40) may be used depending on the intended use of the device. The adhesive (40) may be any medically approved water resistant pressure sensitive adhesive such as hydrocolloid adhesives and hydrogel adhesives. Particularly effective adhesives in providing the desired adhesive properties to secure the flange to the skin of the wearer whilst allowing for relatively painless application and removal are hydrophillic hydrogels formed from crosslinking polymers with a plastisicer to form a 3-dimensional matrix.

The flange (12) is attached to the bag (11) according to any means known to the man skilled in the art which may provide permanent or releasable attachment. Preferably however, the flange is attached to the bag by adhesive. Typically, the bag will be attached to the flange, towards the outer periphery of flange so as not to cause any obstruction for the entering liquids.

The flange (12) may be provided in any size depending on the wearer group for which the device is intended. Similarly the flange (12) may be provided in any shape and preferably has a symmetrical shape preferably at least one lobe (13).

The flange comprises a garment facing portion (22) and a wearer facing portion (23). In an preferred embodiment these are two large, substantially flat surfaces. In a preferred embodiment the wearer facing portion (23) of the flange (12), however, comprises a raised, curved bulge positioned beneath the aperture (21) and extending across the flange (12) for approximately the width of the aperture (21). The bulge is shaped to span the perineum of an infant. Typically urine management devices (10) for female wearer's comprise such a bulge, while urine management devices (10) for mate wearer's do not need to comprise such a bulge.

The flange (12) should be made of soft, flexible and malleable material to allow easy placement of the flange to the uro-genital area. In addition it is preferred that the flange (12) be made of a hydrophobic material such that if urine does come into contact with the perimeter surrounding the aperture (21) it is repelled and does not wick to the outer edge of the flange (12). Typical materials include nonwoven materials, wovens, open celled thermoplastic foams, closed-cell thermoplastic foams, composites of open celled foams and stretch nonwoven, and films. A closed-cell foam of polyethylene has been found effective, but more preferably an open celled polyurethane foam is used. Preferably, such foams have a thickness within the general range of 0.1 to 5 millimetres and a density of 5 to 250 g/m$^2$, more preferably 50 g/m$^2$. Other thermoplastic foam materials, or other suitable plastics sheet materials having the described properties of such foams (i.e., softness, pliability, stretchability, and contractability) might also be used. Preferably, the material of garment facing surface (21) of the flange (12) may extend into the defined aperture area so as to form a skirt or flap of material which prevents unintentional adhesion of the surface edges of the flange (12) defining the aperture (21) to one another during use.

According to the present invention the urine management device further comprises an attachment means to secure the device to the wearer. Such means include straps and more preferably comprises a body-compatible pressure sensitive adhesive (20) applied to the wearer facing portion (23) of the flange (12).

According to the present invention any medically approved water resistant pressure sensitive adhesive may be used to attach the device to the uro-genital area of the wearer, such as hydrocolloid adhesives and hydrogel adhesives. Particularly effective adhesives in providing the desired adhesive properties to secure the flange to the skin of the wearer at the sensitive uro-genital area, whilst allowing for relatively painless application and removal, are formed from crosslinking polymers with a plastisicer to form a 3-dimensional matrix.

Suitable adhesives for use herein are hydrogel adhesives available from 3M and Promeon.

The adhesive (20) can be applied to the wearer facing surface (22) of the flange (12) by any means known in the art such as slot coating, spiral, or bead application or printing. Typically the adhesive (20) is applied at a basis weight of from 20 g/m$^2$ to 2500 g/m$^2$, more preferably from 500 g/m$^2$ to 2000 g/m$^2$ most preferably from 700 g/m$^2$ to 1500 g/m$^2$ depending on the end use envisioned. For example for urine management devices (10) to be used for babies the amount of adhesive (20) may be less than for urine management devices designed for active adult incontinence sufferers.

According to another aspect of the present invention, the urine management device (10) has been found particularly useful and beneficial when utilized in conjunction with a garment or a disposable diaper or a faecal management device. Typically the urine management device (10) will be positioned to the uro-genital area of the wearer positioned and secured to the wearer by the adhesive flanges and patches of adhesives. Subsequently, the diaper is positioned over the urine management device and fastened in a conventional manner around the body of the wearer. It has been found that in addition to providing excellent separation between urine and faecal matter, the combined urine management device (10) and diaper system reduce skin irritation, which may at time occur, especially as the wearer group includes the very old, young and unhealthy wearers.

Detailed Description of the Aperture

To allow a more detailed and clear description of the device (10), in the following paragraphs firstly the terms, as used herein, will be defined.

Regarding in particular the flange (12) the longitudinal axis is to be understood as follows: The direction which is substantially defined by a line connecting the coccyx, the perineum and the genital area for a wearer with the urine management device (10) in the intended wearing position defines the longitudinal direction. The longitudinal axis is an axis in the longitudinal direction, which crosses the centre of the aperture (21). The longitudinal axis is typically also an axis of symmetry.

The transversal axis is an axis perpendicular to said longitudinal axis, which crosses the centre of the aperture (21). The transversal direction is generally aligned with the wearer's hips when the urine management device (10) is in the intended wearing position.

Unbent is used with regard to the flange (12). The flange (12) is typically bent along a longitudinal axis to place it onto the uro-genital area of the wearer. In an unbent state the flange (12) is typically flattest.

Flat is used in the description of a three-dimensional object, such as the flange (12), if the object can be thought to be fully contained by a cuboid, characterised by three characterising lengths, of which one first length is less than half of either of the two other characterising lengths. If the object is flexible in shape, so that it may take several shapes without a substantial effect on its properties or damage, it is called flat if it is flat in one of said shapes. Such an flexible object is in its flattest shape if said first characterising length is minimal.

The contour of the aperture (21) is defined by the inner periphery (25) of the flange (12). References to the contour of the aperture (21) are to be understood with reference to the unbent flange (12), unless otherwise stated. The contour of a flexible aperture (21) is to be understood as the form of the inner periphery (25) of the flange (12) when no outer forces are present which could affect the shape of the aperture (21) (apart from normally unavoidable forces such as gravity). If the aperture (21) is provided with a skirt, this skirt does not define the contour of the aperture (21). Oval aperture (21), for example, and aperture (21) having an oval contour are used interchangeably.

Centre is used to describe a point of an object or a part of an object, which coincides with the centre of mass, if said object or part were of uniform density. Thus for the aperture (21), the centre is to be determined when the area within the contour of the aperture (21) is considered to be filled with a material of uniform thickness and density, when the flange (12) is unbent.

A diameter of the aperture (21) is the length of a line through the centre of the aperture (21), whose ends lie on the inner periphery (25) of the aperture (21), when the flange is unbent. The diameter of a flexible aperture (21) has to be measured when no outer forces are present which could affect the shape of the aperture (21) (apart from normally unavoidable forces such as gravity). The longitudinal diameter of the aperture (21) is measured along the longitudinal axis. The transversal diameter of the aperture (21) is measured along the transversal axis. An oval aperture (21) is referred as oriented in the longitudinal direction if the longitudinal diameter of the aperture (21) is greater than the transversal diameter. An oval aperture (21) is referred as oriented in the transversal direction if the transversal diameter of the aperture (21) is greater than the longitudinal diameter.

The major axis and the minor axis are characterising axes of an ellipses, the major axis being the longest axis of the ellipse and the minor axis being the longest axis perpendicular thereto.

The aperture (21) of the urine management device (10) as used herein is to be understood as the part of the device (10) which receives urine, which is then entrapped in the bag. The aperture (21) does not need to be open, when not receiving urine. For example, the aperture (21) may be closed by a given mechanism, in particular after detachment.

It has now been found that apertures having particular configurations are particularly beneficial in providing ease of application whilst minimizing skin irritation problems. Accordingly the apertures (21) of the present invention are selected from oval apertures, slit like apertures or cross shaped apertures.

The main benefit of an oval aperture (21) oriented in the longitudinal direction, whose longitudinal diameter is at least 2.25 times greater than the transversal diameter, is in the placement of the urine management device (10). The correct placement of the device (10) involves bringing the aperture (21) in registry with the urinary duct of the wearer. The chances for a misplacement in the transversal direction are less than the chances for a misplacement in the longitudinal direction. This is so, particularly for female wearer's, since the anatomy of the crotch region, namely the thighs, supports the correct placement of the device (10) with regard to the transversal direction, but hardly with regard to the longitudinal direction. Thus an oval aperture (21), which is oriented in the longitudinal direction, is desirable to allow for some misplacement in that direction, so that such misplacement will not result in the aperture (21) not covering the urinary duct.

Figure 2:
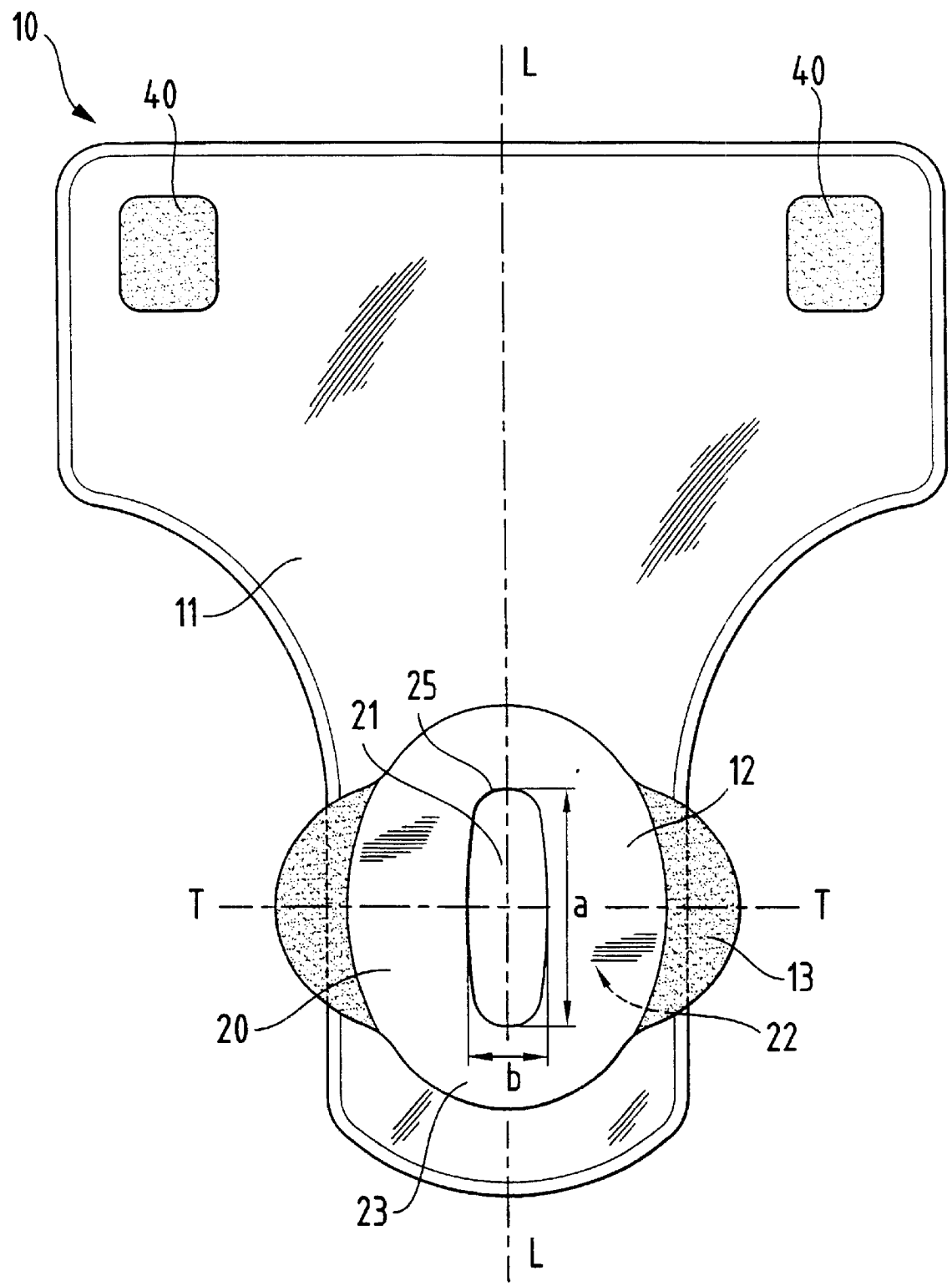
FIG. 2 is a perspective view of another preferred embodiment of the urine management device. L denotes a longitudinal axis, T denotes a transversal axis. a denotes the longitudinal diameter of the aperture, b denotes the transversal diameter of the aperture.

The choice of a particular shape will depend on the intended wearer group and using conditions. The aperture (21) may for example be elliptical in the longitudinal or in the transversal direction. The aperture (21) may also have an essentially elliptical form with flattened ends, e.g. to either side of the major axis as shown in FIG. 2. Preferred flattened elliptical forms have a length along the major axis of 65% to 95%, more preferably around 80%, of the major axis of the corresponding full ellipse. Other flattened elliptical forms have a length along the minor axis of 65% to 95%, more preferably around 80%, of the minor axis of the corresponding full ellipse. The flat portions preferably comprise a straight line. Elliptical forms of the aperture (21), which are flattened to either side of the major axis and to either side of the minor axis are also preferred.

Preferred apertures (21) are also those which are oval without being strictly elliptical in a mathematical sense. In particular, elliptical forms with flattened ends as described above are preferred embodiments of the present invention.

Preferred apertures (21) oriented in the longitudinal direction or oriented in the transversal direction are characterised by a certain ratio between the transversal diameter and the longitudinal diameter. This ratio is from 1:1.25 to 1:20, more preferably from 1:1.25 to 1:10, yet more preferably 1:1.5 to 1:5, even more preferably from 1:1.75 to 1:4, yet more preferably from 1:2 to 1:3, most preferably from 1:2.25 to 1:2.75. Oval apertures of these ratios are particularly preferred if they are oriented in the longitudinal direction. In particular for urine management devices (10) which are designed for female wearer's and which comprise an elliptical aperture the preferred ratios are from 1:1.75 to 1:4, yet more preferably from 1:2 to 1:3, most preferably from 1:2.25 to 1:2.75. Any range of ratios comprising one lower limit and one upper limit listed above is to be considered a preferred range.

In another embodiment the present invention comprises an aperture (21) in form of a slit. This form is preferably not provided by one single cut, but has a substantially rectangular form and a minimal transversal diameter in the range of 0.5 to 100 mm, more preferably 5 mm to 60 mm, yet more preferably 10 mm to 40 mm. Preferably the slit is oriented in the longitudinal direction.

In another preferred embodiment the slit is not rectangular, but comprises straight portions to either side of the longitudinal axis, while comprising curved portions to either side of the transversal axis.

In another embodiment the present invention comprises an aperture (21) in form of a cross. For example, such a cross may be formed by two slits or two ellipses or flattened ellipses as described above, one oriented in the longitudinal direction and one oriented in the transversal direction. Such an aperture (21) is beneficial in particular with regard to male wearers. It has the advantage of providing a large diameter in the longitudinal and in the transversal direction while providing shorter diameters in the direction in-between. In these directions adhesive portions on the flange (12) can be provided close to the urinary duct.

The aperture (21) does not need to have any element of symmetry, however in a preferred embodiment the aperture (21) is symmetrical to the longitudinal axis, and in an even more preferred embodiment the aperture (21), is symmetrical to the longitudinal axis and to the transversal axis. The symmetry of the aperture (21) to the longitudinal axis reflects the substantial symmetry of the human body to the longitudinal axis and thus is typically beneficial for the good anatomical fit of the urine management device (10), as well as for proper adhesion and complete collection of urine. The symmetry of the aperture (21) to the transversal axis may allow the urine management device (10) to be placed to the uro-genital area of the wearer without ensuring a specific orientation regarding the perineal and coccygeal areas of a wearer. Said symmetries typically also allow the easier, cheaper and more accurate production of the flange (12) and may also ensure a more aesthetic appearance of the device (10).

All the embodiments described herein have an aperture (21) as small as possible with regard to the optimal performance of the device (10) for particular wearer groups and uses. Thus, the risk of skin irritation due to contact of urine with the skin of the wearer is as far as possible reduced. Furthermore it is a particular advantage if the apertures (21) described herein provide a large surface area of the flange (12) close to the centre of the aperture (21) while not hindering the urination process and thereby still allowing effective collection of urine. The presence of such large areas of the flange (12) close to the centre of the aperture (21) is very beneficial, as it allows for a more secure attachment of the urine management device (10) by adhesive provided on the wearer facing portion (23) of the flange (12).

If the aperture (21) is oriented in the longitudinal direction the transversal diameter is preferably less than 60%, more preferably less than 50%, yet more preferably less than 40%, most preferably less than 30% of the diameter of the flange (12) in the transversal direction and the longitudinal diameter is preferably more than 50%, more preferably more than 55%, yet more preferably more than 60%, still more preferably more than 70%, most preferably more than 80% of the diameter of the flange (12) in the longitudinal direction. If the aperture (21) is oriented in the longitudinal direction, the transversal diameter is preferably less than 2.5 cm, more preferably less than 2.0 cm, still more preferably less than 1.5 cm, most preferably less than 1.0 cm and the longitudinal diameter is preferably more than 2.5 cm, more preferably more than 3.0 cm, yet more preferably more than 3.5 cm, still more preferably more than 4.5 cm, most preferably 5.0 cm.

What is claimed is:

1. A urine management device comprising a bag said bag having an aperture and a flange surrounding said aperture, said aperture having a contour and a longitudinal and a transversal direction and a longitudinal diameter and a transversal diameter. said contour being selected from:
   a) a slit like contour,
   b) an oval contour oriented in said transversal direction, wherein said transversal diameter of the aperture is at least 1.25 times greater than said longitudinal diameter,
   c) an oval contour oriented in said longitudinal direction, wherein said longitudinal diameter of the aperture is at least 1.25 times greater than said transversal diameter,
   d) a cross shaped contour,
wherein said contour of said aperture is defined by one ellipse, said ellipse having a major axis and a minor axis, wherein said major axis is in said longitudinal or said transversal direction and, wherein said aperture is oval and oriented in the longitudinal direction and said longitudinal diameter of said aperture is at least 60% of the longitudinal diameter of the flange.

2. A urine management device comprising a bag said bag having an aperture and a flange surrounding said aperture, said aperture having a contour and a longitudinal and a transversal direction and a longitudinal diameter and a transversal diameter, said contour being selected from:
   a) a slit like contour,
   b) an oval contour oriented in said transversal direction, wherein said transversal diameter of the aperture is at least 1.25 times greater than said longitudinal diameter,
   c) an oval contour oriented in said longitudinal direction, wherein said longitudinal diameter of the aperture is at least 1.25 times greater than said transversal diameter,
   d) a cross shaped contour,
wherein said contour of said aperture is defined by one ellipse, said ellipse having a major axis and a minor axis, wherein said major axis is in said longitudinal or said transversal direction and, wherein said aperture is oval and oriented in the longitudinal direction and said longitudinal diameter of said aperture is at least 3.5 cm.

* * * * *